United States Patent
Becker

Patent Number: 6,085,741
Date of Patent: *Jul. 11, 2000

[54] DEVICE FOR ATOMISATION OF FLUIDS

[75] Inventor: Rudolf Becker, Starnberg, Germany

[73] Assignee: PARI GmbH Spezialisten für effektive Inhalation, Starnberg, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/848,950

[22] Filed: Apr. 30, 1997

Related U.S. Application Data

[63] Continuation of application No. 08/658,269, Jun. 6, 1996, abandoned.

[30] Foreign Application Priority Data

Jun. 6, 1995 [DE] Germany .......................... 195 20 622

[51] Int. Cl.⁷ .................................................. A61M 16/00
[52] U.S. Cl. .............................. 128/200.21; 128/200.14; 128/203.12; 128/203.16; 239/338
[58] Field of Search ........................ 128/200.21, 200.18, 128/200.11, 200.14, 203.12, 203.15, 203.16, 204.14, 203.25, 205.11; 239/338, 370

[56] References Cited

U.S. PATENT DOCUMENTS

| | | | |
|---|---|---|---|
| 2,603,215 | 7/1952 | Arnow | 128/203.15 |
| 3,534,739 | 10/1970 | Bryne | 128/200.14 |
| 3,658,059 | 4/1972 | Steil | 128/200.21 |
| 4,588,129 | 5/1986 | Shanks et al. | 128/200.18 |
| 4,657,007 | 4/1987 | Carlin et al. | 128/200.21 |
| 4,674,491 | 6/1987 | Brugger et al. | 128/200.18 |
| 4,805,609 | 2/1989 | Roberts et al. | 128/200.21 |
| 5,209,225 | 5/1993 | Glenn | 128/200.21 |
| 5,280,784 | 1/1994 | Köhler | 128/203.12 |
| 5,312,046 | 5/1994 | Knoch et al. | 128/200.18 |
| 5,318,015 | 6/1994 | Mansson et al. | 128/200.21 |
| 5,503,139 | 4/1996 | McMahon et al. | 128/200.18 |
| 5,549,102 | 8/1996 | Lintel et al. | 128/200.21 |
| 5,584,285 | 12/1996 | Salter et al. | 128/200.21 |

*Primary Examiner*—John G. Weiss
*Assistant Examiner*—V. Srivastava
*Attorney, Agent, or Firm*—Merchant & Gould P.C.

[57] ABSTRACT

The invention relates to a device for atomising fluids and having a bottom part (1) and a top part (2) disposed so as to be axially symmetrical with the bottom part, and comprising an intake air arrangement (3) and an outlet nozzle (4). The atomiser according to the invention also has an insert (5) for receiving a fluid (23) and a nozzle arrangement (6) disposed so as to be axially symmetrical with the intake air arrangement (3). The intake air arrangement (3) has a hollow cylindrical duct (7) with a conical widening (8) towards the incoming air end. As a result of being constructed according to the invention, the atormiser is particularly suitable for local inhalation anaesthesia, e g. in preparation for examination of the bronchi.

18 Claims, 3 Drawing Sheets

DEVICE FOR ATOMISATION OF FLUIDS

This is a Continuation of application Ser. No. 08/658,269, filed Jun. 6, 1996 abandoned.

The invention relates to a device for atomising fluids.

Devices used for inhalation therapy are known in medical technology. Inhalation devices of this kind operate e.g. with a spray diffuser having a tapering bore. A gaseous pressure medium under pressure leaves the bore, so as to suck a fluid drug out of suction ducts disposed near the nozzle bore. The sucked fluid drug is thrown against a baffle surface of a gas flow control disposed opposite the nozzle mouth in the outlet cone of the compressed gas, so that aerosol droplets are produced. The aerosol droplets then flow against a deflecting screen, which additionally breaks up the larger aerosol particles so as to obtain intrathoracal particles, i.e. small enough to enter the lung, measuring about 0.5 to 5 $\mu$m.

A nozzle atomiser of this kind is known e.g. from EP-A-0 170 715.

However, since nozzle atomisers of this kind produce aerosol particles of 5 $\mu$m or less in diameter, they are unsuitable for applications requiring larger-diameter droplets. One example of such an application is to local inhalation anaesthesia, used e.g. during examinations of the bronchi. In this case, in contrast to inhalation therapy, much larger aerosol particles are required with a high output.

Ultrasonic inhalers using a spray through ultrasound are also known in the prior art. The disadvantage of ultrasonic atomisers, however, is that the medium exposed to ultrasonic waves is subjected to alteration mainly through cavitation, which may be sufficient to destroy the medium. The effect of cavitation, for example, may be to destroy molecule chains in drugs, since ultrasound has a strong local effect on the drug. This alters the properties of the drug, which is unacceptable for use in anaesthetics.

The object of the invention is to provide a device for atomisation of fluids which produces droplets in a range suitable for local inhalation anaesthesia.

This problem is solved by the features of the independent claim. The dependent claims disclose advantageous embodiments and additional features of the invention.

The device according to the invention for atomising fluids has a bottom part releasably connected to a top part. The two parts are disposed so as to be axially symmetrical with one another. An insert for receiving a fluid can be pressed into the bottom part. The fluid is e.g. an anaesthetic for local inhalation anaesthesia. The top part contains an intake air arrangement and an outlet nozzle for the aerosol droplets which are produced. The intake air arrangement is axially symmetrical with the top part of the atomiser and substantially comprises a hollow cylindrical duct which widens conically towards the air inlet end. A nozzle arrangement is releasably disposed in the insert and is axially symmetrical with the intake air arrangement.

Owing to the construction of the atomiser according to the invention, a range of aerosol particles having a medial mass-diameter distribution with a maximum at 8.5 $\mu$m can be obtained at the outlet nozzle of the top part of the atomiser. The resulting aerosol droplets do not enter the lung but are deposited in the throat, the glottis and the bronchi. Consequently, local inhalation anaesthesia with high efficiency can be obtained during examination of the bronchi. In addition, by means of an interval key, the anaesthetic can be delivered in metered proportions. This avoids losses, since the preparation is atomised only when the patient is inhaling. Optionally also, the parts of the atomiser are made of temperature-resistant plastic, so that the atomiser can be completely sterilised and boiled and has resistance to washing machines.

Also, the insert used as a measuring beaker can be replaced, and can be used for different atomisers. Consequently a measuring beaker can always be filled with the same drug, thus making it easier to handle the device.

According to the invention, therefore, the nozzle arrangement, the insert and the top part of the atomiser comprising the intake air arrangement and the outlet nozzle are arranged relative to one another so as to produce a range of droplets specifically indicated and very suitable for local inhalation anaesthesia, e.g. for examining the bronchi.

Embodiments of the invention will now be explained in detail with reference to the accompanying drawings, in which.

Figure 1:
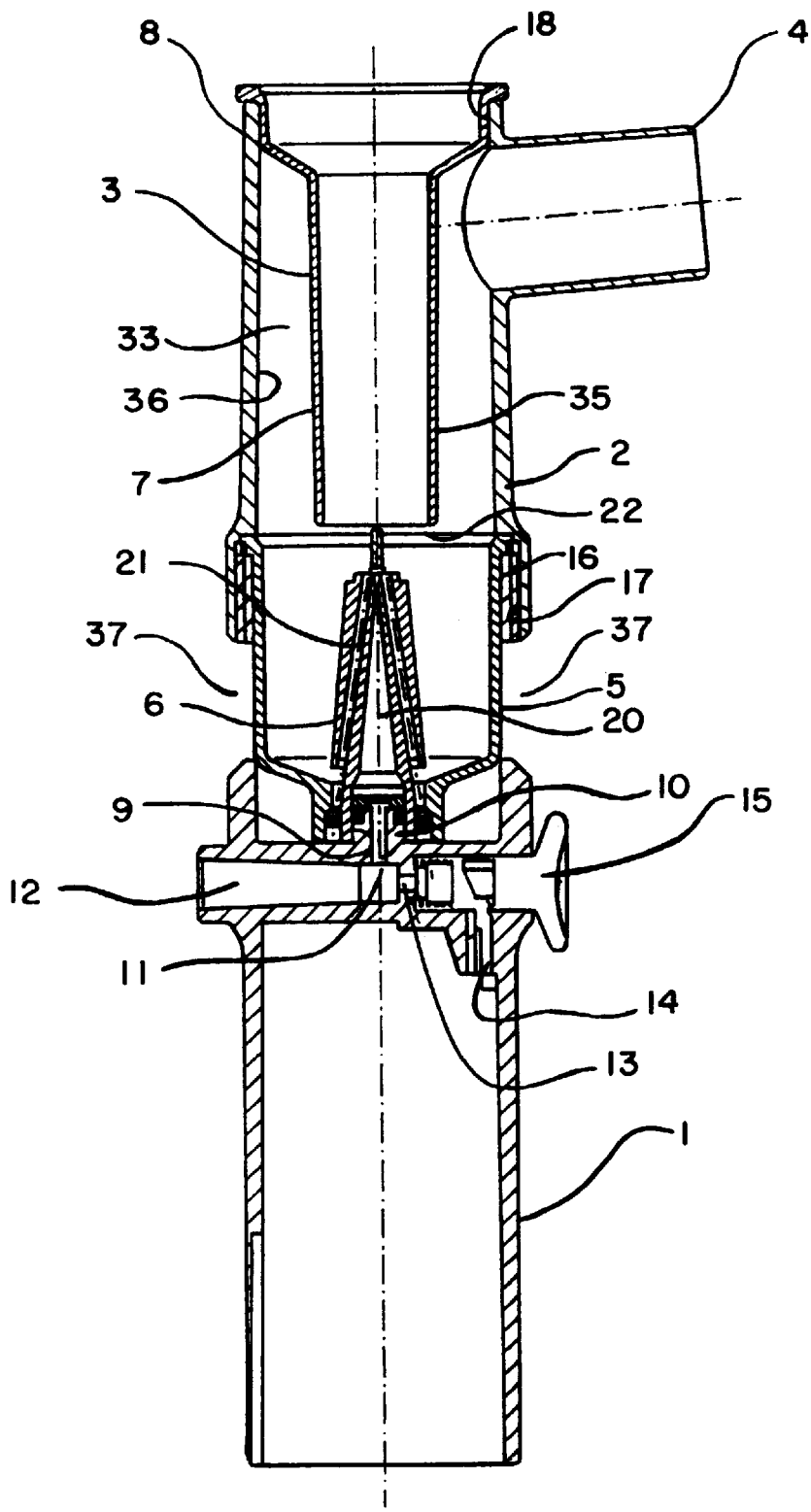
FIG. 1 shows an embodiment, partly in section, of an atomiser according to the invention.

FIG. 1 shows an atomiser with a bottom part 1 and a top part 2. An insert 5 is disposed for insertion into a top portion of the bottom part 1. The insert 5 is used inter alia as a beaker for drugs. The insert 5 contains a nozzle arrangement 6. The nozzle arrangement 6 has a bore 9 in engagement with a spigot 10. The spigot 10 has an inner bore 11 connected to a supply duct 12 for compressed air. The supply duct 12 is connected by a bore 13 to an air outlet opening 14. An interval key 15 provided in the bottom part 1 can close the air outlet opening 14, so that compressed air supplied through the duct 12 flows through the inner bore 11 of the spigot 10 to a compressed-air duct 20 in the nozzle arrangement 6.

The upper portion of the bottom part of the atomiser has e.g. two openings 37, giving a view of the insert or drug beaker S. Since the drug beaker is preferably made of a transparent material, the level of fluid in the beaker can be checked.

The top part 2 of the atomiser has an intake air arrangement 3 comprising a hollow cylindrical duct 7 at the air outlet end of the intake air arrangement 3 and a conical widening 8 at the air inlet end of the intake air arrangement 3. The top part 2 is also integral with a hollow cylindrical outlet nozzle 4 which can be connected to a mouthpiece (not shown), through which the patient can inhale the droplets of aerosol produced by the nozzle arrangement 6.

Owing to the advantageous construction of its parts, the atomiser according to the invention can easily be put together or assembled. Beginning e.g. with the bottom part 1 and the already-provided interval key 15, the insert 5 with the inserted nozzle arrangement 6 can be mounted on the spigot 10 or inserted into the upper portion of the bottom part 1. The insert 5 can be filled with the appropriate anaesthetic before being inserted into the bottom part 1, or alternatively a metered amount of anaesthetic can be poured into the insert 5 after insertion.

Next, the top part 2 of the atomiser can be secured to the bottom part 1. The connection can be by screwing, an outer thread 16 on the bottom part 1 engaging an inner thread 17 on the top part 2. The top part 2 comprises the intake air arrangement 3, which is releasably inserted into the top part 2. The inserted intake air arrangement 3, when in the assembled state, is positively connected to a portion of the widening 8, via an inner peripheral portion 18 of the top part 2. The outlet nozzle 4 is disposed in an upper region of the top part 2 and slopes upwards preferably at an angle of about 5° from a normal to the axis of symmetry of the top part 2. The mouthpiece (not shown) can then be slid over the outlet nozzle 4.

When the atomiser is in operation, compressed air is supplied to the duct 12. When the interval key 15 is not actuated, the supplied compressed air flows out of the air outlet opening 14. When the interval key 15 is actuated, the supplied compressed air flows through the compressed-air duct 20 of the nozzle arrangement 6 and out through a nozzle 38 in the nozzle arrangement 6 (see FIG. 2). The compressed air flowing out of the nozzle 38 is deflected by a gas flow control 19 so as to produce a negative pressure in the suction ducts 21 of the nozzle arrangement 6. A bottom end 34 of the suction duct 21 opens into a lower region of the insert 5. During operation the insert 5 is filled with fluid so that the bottom end 34 of the suction duct 21 is covered with fluid. As a result of the negative pressure occurring at the top end 35 of the suction duct 21, fluid is sucked from the insert 5 into the suction duct 21 and finely divided by the compressed air coming out through the nozzle 38. The resulting aerosol particles preferably have a median mass-diameter distribution with a maximum at 40 μm. The aerosol particles are then further reduced in size e.g. by striking a bottom collar 22 on the hollow cylindrical duct 7 and by rebounding from the outer wall of the hollow cylindrical duct 7 and the inner wall of the top part 2.

In order to inhale the resulting aerosol particles, the patient uses the mouthpiece to generate a negative pressure at the outlet nozzle 4, so that air flows through the intake air arrangement 3 downwards in the direction towards the nozzle arrangement 6. The air then flows through an annular duct 33 upwards to the outlet nozzle 4. The annular duct 33 is substantially formed by an outer surface 35 of the inlet air arrangement 3 and an inner surface 36 of the top part 2 of the atomiser.

As a result of the geometrical shape and arrangement of the individual components relative to one another, more particularly the nozzle arrangement 6, the intake air arrangement 3, the inner wall of the top part 2 and the outer wall of the outlet nozzle 4, aerosol droplets are produced with a median mass-diameter distribution having a maximum preferably at 8.5 μm. As a result the atomiser according to the invention is particularly suitable for local inhalation anaesthesia, e.g. for the purpose of examining the bronchi.

It is found that with the chosen shape, the compressed gas advantageously is at an excess pressure of $1.1 \times 10^5$ Pa, with the result that a total output of about 800 mg/min can be obtained.

Figure 2:
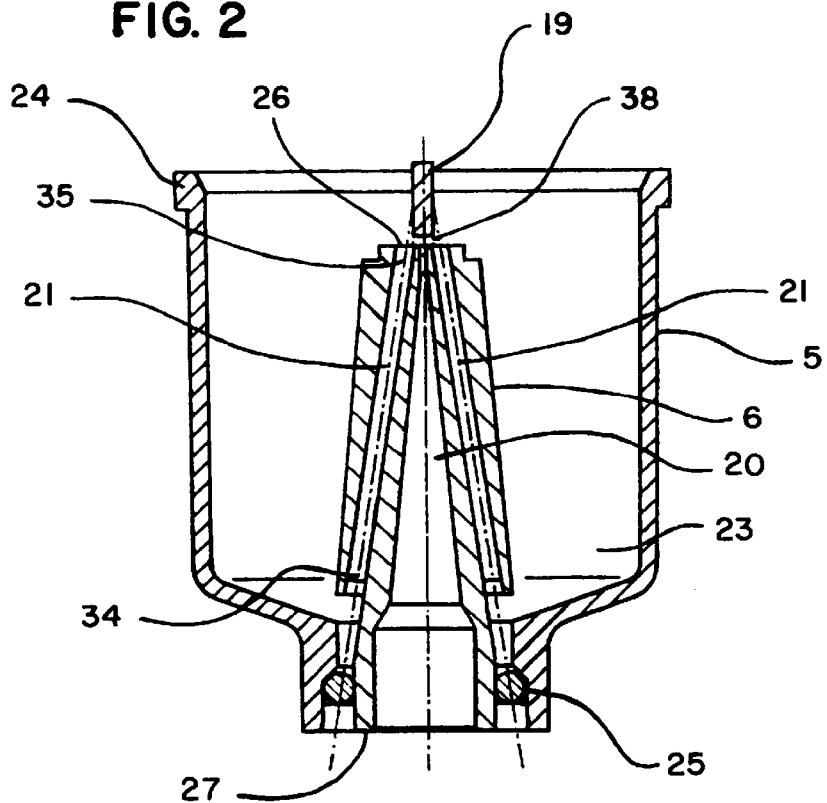
FIG. 2 is a cross-sectional view of an embodiment of a beaker for drugs according to the invention, fitted with a nozzle arrangement.

FIG. 2 is a larger-scale view of the insert 5 and the nozzle arrangement 6. The insert 5 is partly filled with a fluid 23. The fluid 23 is e.g. the anaesthetic for use. As shown in FIG. 2, during operation the upper edge of the fluid 23 is situated above the lower openings 34 in the intake ducts 21. The fluid 23 can thus be sucked into the ducts 21, and then comes out through corresponding openings 26 at the top. The fluid 23 is then atomised by the flow of gas from the nozzle 38 and deflected by the gas flow control 19. The drug beaker, in the state when inserted into the top part 2, is situated above a step 24 on the top edge of the bottom part of the atomiser. The insert 5 is also in contact with the bottom part 1 via a bottom abutment surface 27. The nozzle arrangement 6 is disposed so as to be axially symmetrical with the insert 5. An O-ring 25 is disposed between the nozzle arrangement 6 and the insert 5. The O-ring 25 seals the nozzle arrangement 6 against the insert 5.

Figure 3:
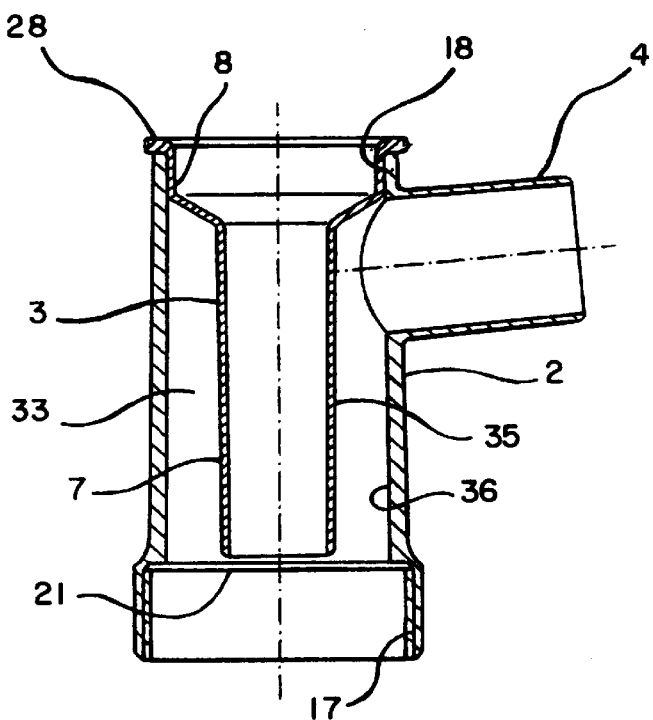
FIG. 3 is a cross-sectional view of an embodiment of a top part of an atomiser according to the invention, with an intake air arrangement and an outlet nozzle

FIG. 3 shows the top part 2 of the atomiser. The top part 2 is substantially cylindrical and has an inner thread 17 at its bottom end. The intake air arrangement 3 is in positive engagement with the inner peripheral portion 18 of the top part 2 via a conical widening 8. At the top and, the intake air arrangement 3 has a projecting part 28 abutting the top edge of the top part 2 of the atomizer. The intake air arrangement 3 can thus be inserted into the top part 2, and is brought into a defined position by the projecting part 28. In the inserted state, the intake air arrangement 3 is axially symmetrical with the top part 2. The nozzle 4 is integrally formed on the top part 2. As a result of the hollow cylindrical duct 7 in the intake air arrangement 3, the annular duct 33 is formed between the outer surface 35 of the hollow cylindrical duct 7 and the inner surface 36 of the top part 2 of the atomiser. The fluid-mechanical processes occurring in this annular flow space are of help in producing the preferred aerosol droplet diameter. The dimensions of these components are chosen so that the ratio, taken at a medium height, of the inner diameter of the top part 2 to the outer diameter of the hollow cylindrical duct 7 is preferably about 1.8. The wall thickness of the hollow cylindrical duct 7 can be about 1 mm and its inner diameter about half way up can be 1.45 mm. The hollow cylindrical duct 7 can be about 4.6 mm long and can taper slightly conically towards the air outlet end.

Figure 4:
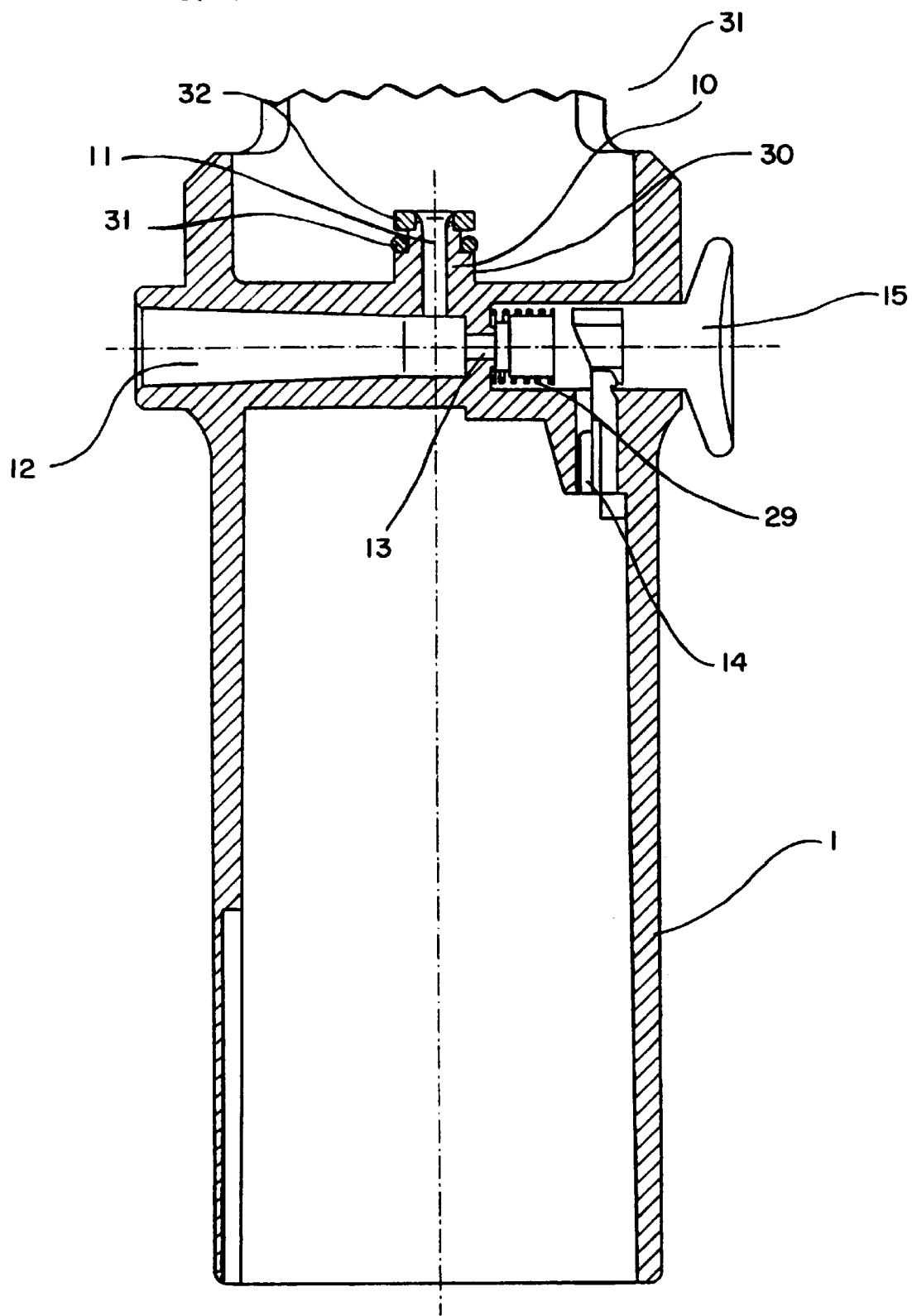
FIG. 4 is a partly sectional view of an embodiment of a bottom part of an atomiser according to the invention with an interval key.

FIG. 4 shows the bottom part 1 of the atomiser, another portion of which is substantially a hollow cylinder. The top portion of the bottom part 1 contains the interval key 15. The duct 12 for supplying compressed air is provided opposite the interval key 15. The duct is connected to the inner bore 11 of the spigot 10 and also to a connecting bore 13 to the air outlet opening 14. When the interval key 15 is not being actuated, it is pressed by a spring 29 outwards up to an abutment, so that a connection for fluid is made between the duct 12, the bore 13 and the air outlet opening 14. When the key 15 is pressed, the air outlet opening 14 or the connecting bore 13 is closed, so that the pressure medium flowing into the duct 12 flows through the inner bore 11 into the spigot 10 and consequently into the nozzle arrangement 6. The spigot 10 has a step 30 in which an O-ring 31 is disposed. When the arrangement shown in FIG. 2 is mounted on the spigot 10 (compare FIG. 1) the O-ring 31 seals the nozzle arrangement 21 against the spigot 10. An annular locking washer 32 is also formed on the spigot 10 at the top. The washer 32 secures the O-ring 31 so that it does not slide off the spigot when the nozzle arrangement 6 is pulled off, and the washer also locks the nozzle arrangement 6, when inserted.

The atomiser according to the invention is particularly suitable for use in local inhalation anaesthesia, since it produces aerosol particles having a diameter such that they are deposited in the throat, glottis and the bronchial space. The droplets produced have a size which does not enter the lungs, since such a range of droplets is unsuitable for inhalation anaesthesia. Owing to the specific indicated droplet range, the device according to the invention is of preferred use in preparation for bronchial examinations, and the atonmiser as described is of preferred use for local inhalation anaesthesia in preparation for an operation.

What is claimed is:

1. A device for atomizing fluids for inhalation, comprising:
   a top portion having a generally cylindrical body with an open top end, an open bottom end and a sidewall, with an atomized fluid outlet defined in the sidewall;

a generally cylindrical air intake duct extending from the top end of the cylindrical body toward the bottom end of the cylindrical body, positioned substantially coaxially with the cylindrical body and having a smaller diameter than that of the cylindrical body so as to define an annular passage between an outer surface of the air intake duct and an inner surface of the cylindrical body for delivery of atomized fluid to the outlet, said air intake duct having a top end defining an air inlet opening and a bottom end defining an air outlet opening;

an atomizing nozzle positioned substantially coaxially with the air intake duct near the air outlet opening, the atomizing nozzle being adapted for communication with a source of compressed gas;

an insert for supplying fluid to be atomized to the nozzle, positioned adjacent the bottom end of the top portion; and a generally cylindrical bottom portion for maintaining the insert in position, positioned substantially coaxially with the top portion wherein the top portion and the air intake duct have a length and diameter such that atomized fluid particles having a size suitable for delivery to a vicinity of bronchia, throat and glottis of a patient are delivered to the atomized fluid outlet via the annular passage upon inhalation by a patient through the atomized fluid outlet.

2. A device according to claim 1, wherein the top end of the air intake duct has a diameter substantially equal to that of the cylindrical body and further comprises a reduced diameter lower section and a conical section connecting the top end and the lower section.

3. A device according to claim 1, wherein the bottom portion is releasably secured to the top portion.

4. A device according to claim 3, wherein the insert is substantially cylindrical and is releasably carried by the bottom portion so as to be positioned substantially coaxially with the bottom portion, and the nozzle is releasably carried by the insert.

5. A device according to claim 4, wherein the bottom portion comprises a spigot for carrying compressed gas, the nozzle comprising a bore communicating with the spigot.

6. A device according to claim 5, wherein the bottom portion comprises a compressed gas supply passage, and the spigot comprises an inner bore communicating with the compressed gas supply passage, the bottom portion further comprising a control for interrupting a flow of compressed gas in the compressed gas supply passage to the spigot.

7. A device according to claim 4, wherein the insert is at least partly transparent and the bottom portion has an opening providing a view of the insert.

8. A device according to claim 1, wherein the nozzle comprises two suction ducts for carrying fluid to be atomized and also comprises a gas flow control member positioned at a top portion of the nozzle, the nozzle aerosol particles having a median mass-diameter distribution with a maximum of about 40 $\mu$m.

9. A device according to claim 1, wherein the atomized particles delivered through the atomized fluid outlet have a median mass-diameter distribution with a maximum of about 8.5 $\mu$m.

10. A method of delivering an active agent in the form of an atomized fluid to a vicinity of bronchi, throat and glotti of a patient, comprising:

forming an atomized fluid containing an active agent to be delivered to a patient in a device for atomizing fluids for inhalation, said device comprising:

a top portion having a generally cylindrical body with an open top end, an open bottom end and a sidewall, with an atomized fluid outlet defined in the sidewall;

a generally cylindrical air intake duct extending from the top end of the cylindrical body toward the bottom end of the cylindrical body, positioned substantially coaxially with the cylindrical body and having a smaller diameter than that of the cylindrical body so as to define an annular passage between an outer surface of the air intake duct and an inner surface of the cylindrical body for delivery of atomized fluid to the outlet, said air intake duct having a top end defining an air inlet opening and a bottom end defining an air outlet opening;

an atomizing nozzle positioned substantially coaxially with the air intake duct near the air outlet opening, the atomizing nozzle being adapted for communication with a source of compressed gas;

an insert for supplying fluid to be atomized to the nozzle, positioned adjacent the bottom end of the top portion; and a generally cylindrical bottom portion for maintaining the insert in position, positioned substantially coaxially with the top portion wherein the top portion and the air intake duct have a length and diameter such that atomized fluid particles having a size suitable for delivery to a vicinity of bronchia, throat and glottis of a patient are delivered to the atomized fluid outlet via the annular passage upon inhalation by a patient through the atomized fluid outlet; and delivering the atomized fluid to the patient through the atomized fluid outlet by inhalation.

11. A method according to claim 10, wherein the atomized particles delivered through the atomized fluid outlet have a median mass-diameter distribution with a maximum of about 8.5 $\mu$m.

12. A method according to claim 10, wherein the top end of the air intake duct has a diameter substantially equal to that of the cylindrical body and further comprises a reduced diameter lower section and a conical section connecting the top end and the lower section.

13. A method according to claim 10, wherein the bottom portion is releasably secured to the top portion.

14. A method according to claim 13, wherein the insert is substantially cylindrical and is releasably carried by the bottom portion so as to be positioned substantially coaxially with the bottom portion, and the nozzle is releasably carried by the insert.

15. A method according to claim 14 wherein the bottom portion comprises a spigot for carrying compressed gas, the nozzle comprising a bore communicating with the spigot.

16. A method according to claim 15, wherein the bottom portion comprises a compressed gas supply passage, and the spigot comprises an inner bore communicating with the compressed gas supply passage, the bottom portion further comprising a control for interrupting a flow of compressed gas in the compressed gas supply passage to the spigot.

17. A method according to claim 10, wherein the active agent is a local anesthetic.

18. A method according to claim 17, which is carried out prior to examination of the patient's bronchi.

\* \* \* \* \*